United States Patent
Davics et al.

(10) Patent No.: US 7,007,331 B2
(45) Date of Patent: Mar. 7, 2006

(54) ELECTRIC TOOTHBRUSHES HAVING A MOVING VIEWING SURFACE

(75) Inventors: Nicola Mills Davics, Reading (GB); Frank Delmar Macaulay, Cincinnati, OH (US); Douglas A. Gall, Strongsville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/701,958

(22) Filed: Nov. 5, 2003

(65) Prior Publication Data

US 2005/0091768 A1 May 5, 2005

(51) Int. Cl.
- A46B 13/00 (2006.01)
- B25F 5/00 (2006.01)
- G03B 25/00 (2006.01)

(52) U.S. Cl. .............................. 15/22.1; 15/4; 15/22.2; 15/105; 352/99; 40/430

(58) Field of Classification Search ................ 15/4, 15/21.1, 22.1, 22.2, 22.4, 28, 105; D4/108; 132/120; 352/87, 99, 101–103; 40/430, 495; 446/73, 219, 472; 16/412

See application file for complete search history.

(56) References Cited

U.S. PATENT DOCUMENTS

| | | | | |
|---|---|---|---|---|
| 2,838,976 A | * | 6/1958 | Berger et al. ............... | 352/102 |
| 3,006,111 A | | 10/1961 | Koch | |
| 3,168,315 A | | 2/1965 | Bookman | |
| 3,588,936 A | * | 6/1971 | Duve .......................... | 15/22.1 |
| 4,397,055 A | * | 8/1983 | Cuchiara .................... | 15/22.1 |
| 4,757,986 A | | 7/1988 | Hwang et al. | |
| 4,827,642 A | | 5/1989 | Chatten | |
| 5,070,567 A | * | 12/1991 | Holland ...................... | 15/28 |
| 5,170,525 A | * | 12/1992 | Cafaro ........................ | 15/28 |
| 5,416,942 A | * | 5/1995 | Baldacci et al. ............. | 15/22.1 |
| 5,617,601 A | | 4/1997 | McDougall | |
| 5,617,603 A | * | 4/1997 | Mei ............................ | 15/22.1 |
| 5,732,432 A | * | 3/1998 | Hui ............................ | 15/22.1 |
| 5,867,856 A | * | 2/1999 | Herzog ....................... | 15/22.4 |
| 5,974,615 A | * | 11/1999 | Schwarz-Hartmann et al. ........................... | 15/22.4 |
| 6,032,313 A | * | 3/2000 | Tsang ......................... | 15/22.1 |
| 6,178,579 B1 | * | 1/2001 | Blaustein et al. ............ | 15/28 |
| 6,183,336 B1 | * | 2/2001 | Coleman et al. ............ | 446/267 |
| 6,202,242 B1 | * | 3/2001 | Salmon et al. .............. | 15/22.1 |
| 2003/0017874 A1 | | 1/2003 | Jianfei et al. | |
| 2003/0163881 A1 | * | 9/2003 | Driesen et al. ............. | 15/22.1 |
| 2004/0187889 A1 | * | 9/2004 | Kemp et al. ................ | 132/311 |

FOREIGN PATENT DOCUMENTS

WO    WO 2004/024016 A2    3/2004

* cited by examiner

Primary Examiner—John Kim
Assistant Examiner—Laura C Cole
(74) Attorney, Agent, or Firm—James C. Vago; Karen F. Clark

(57) ABSTRACT

An electric toothbrush is provided. The electric toothbrush includes a handle having a motor disposed therein and a head having one or more moving bristle holders, wherein the one or more moving bristle holders are operatively connected to the motor. A neck disposed is between the handle and the head. The handle has a viewing window and a movable viewing surface disposed there beneath, wherein at least a portion of the viewing surface is visible through the window. The viewing surface is mechanically coupled to the motor so that rotational output of the motor causes movement of the viewing surface. The viewing surface may be directly or indirectly coupled to the motor.

19 Claims, 5 Drawing Sheets

ELECTRIC TOOTHBRUSHES HAVING A MOVING VIEWING SURFACE

FIELD OF THE INVENTION

The invention relates to the field of electric toothbrushes, and more particularly, the invention relates to field of electric toothbrushes having a movable viewing surface.

BACKGROUND OF THE INVENTION

Electric toothbrushes having one or moving bristle holders are known in the art. There is a desire however to provide electric toothbrushes that use the motor output to move structures in addition to the bristle holders, such as a viewing surface having one or more images thereon. The moving images can improve the appeal of the toothbrush for a user, particularly a child, and can encourage use of the electric toothbrush.

BRIEF SUMMARY OF THE INVENTION

An electric toothbrush is provided. The electric toothbrush comprises a handle having a motor disposed therein and a head having one or more moving bristle holders, wherein the one or more moving bristle holders are operatively connected to the motor. A neck disposed is between the handle and the head. The handle has a viewing window and a movable viewing surface disposed there beneath, wherein at least a portion of the viewing surface is visible through the window. The viewing surface is mechanically coupled to the motor so that rotational output of the motor causes movement of the viewing surface. The viewing surface may be directly or indirectly coupled to the motor.

BRIEF DESCRIPTION OF THE DRAWINGS

It is believed that the present invention will be better understood from the following description taken in conjunction with the accompanying drawings in which.

DETAILED DESCRIPTION OF THE INVENTION

Figure 1:
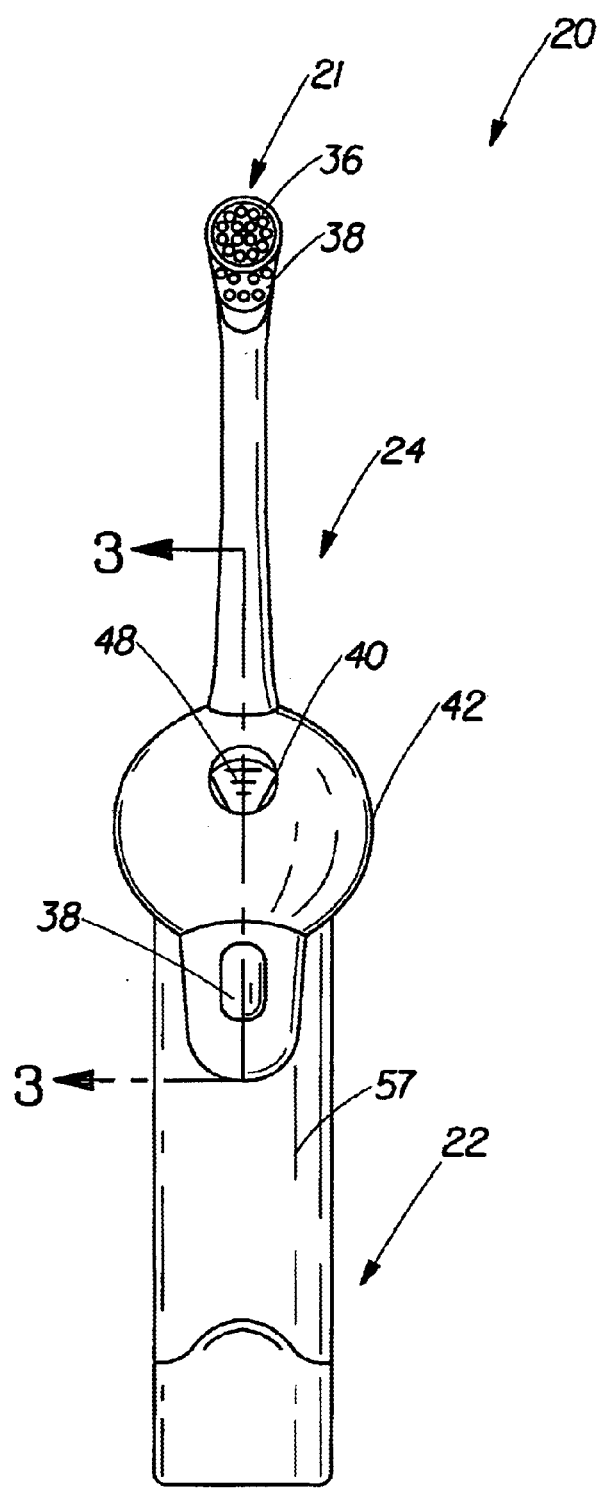
FIG. 1 is a planar top view of an electric toothbrush made in accordance with the present invention.
Figure 2:
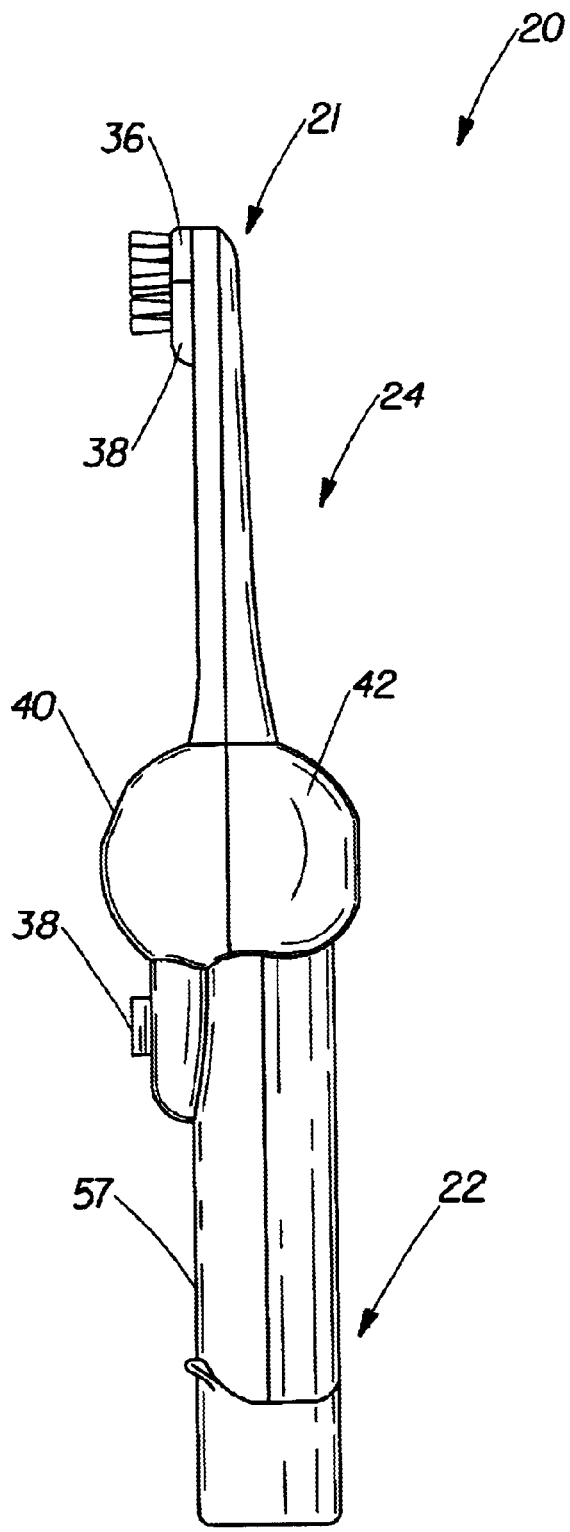
FIG. 2 is a side elevational of the toothbrush of FIG. 1.

All patent publications discussed herein are fully incorporated herein by reference. Reference will now be made in detail to various embodiments of the present invention, examples of which are illustrated in the accompanying drawings wherein like numerals indicate the same elements throughout the views. As will be appreciated, the present invention is directed to electric toothbrushes (including electric toothbrushes having replaceable heads) having a movable viewing surface in addition to one or more moving bristle holders. The movable viewing surface may be indirectly or directly coupled to the motor of the toothbrush. Direct mechanical coupling is intended to refer to physically interconnected elements (e.g., interconnected by pins, adhesives, welding, shafts, fasteners, gears, etc.) and indirect mechanical coupling is intended to refer to interconnected elements that incorporate non-physical connections, such as magnetics.

Referring to FIGS. 1 to 4, an electric toothbrush made in accordance with the present invention will now be described. This electric toothbrush utilizes a shaft that linearly reciprocates along the longitudinal axis of the toothbrush. While the present invention will be described with respect to the particular motor and shaft arrangement illustrated in FIG. 1 for purposes of simplicity and clarity, it will be appreciated that other shaft, gearing, and/or motor arrangements can be substituted. For example, U.S. Pat. Nos. 2003/0163881, 5,617,603; 5,850,603; 5,974,615; 6,032,313; 5,732,432; 5,070,567; 5,170,525; 5,416,942; 3,588,936; 5,867,856; and 4,397,055 illustrate shaft, gearing, and/or motor arrangements that might be suitable.

The electric toothbrush 20 comprises a toothbrush head 21, a body or handle 22, and an elongated neck 24 extending there between. The handle is hollow and includes a motor 26 (FIG. 3) and batteries (not shown) for powering the motor. The motor provides a rotational output via the output shaft 23. A rechargeable power source can be substituted for the batteries. A shaft 34 is housed at least partially within neck 24 and is operatively connected to one or more movable bristle holders. A first movable bristle holder 36 is disposed at a first end of the head 21, wherein the first end is at the forward most point of the head 21. While the first bristle holder 36 is illustrated as circular in shape, other shapes can be utilized. Further, while the first bristle holder 36 is disposed at the first end of the head 21, it will be appreciated that it can be disposed away from the first end and other features, such as stationary bristles, might be disposed between the first bristle holder 36 and the first end of the head 21. The moving bristle holder 36 and the shaft can be interconnected using structures known in the art, such as shown in U.S. Pat. No. 6,178,579. A second bristle holder 38 may be disposed adjacent the first bristle holder 36. The second bristle holder 38 may also move or could be static or fixed.

The bristle holders can undergo any type of motion, including, but not limited to, rotation, oscillation, reciprocation, vibration, gyration, orbital motion, and combinations thereof. As used herein, the term "rotate" is intended to refer to a unidirectional angular motion (e.g., a constant clockwise motion) while the term "oscillate" is intended to refer to vibratory angular motion (e.g., repeated cycles of clockwise rotation and counter clockwise rotation). Vibration is any periodic movement having repeated cycles. Vibratory motion can have one or more frequencies and amplitudes. Vibratory motion that is substantially linear is-referred to herein as a reciprocating motion. The present invention can be used in combination with electric toothbrushes and electric toothbrush heads that include shafts that are operatively connected to the moving bristle holder(s) and which rotate, oscillate, orbit, or reciprocate (as well as combinations thereof) to impart motion to the bristle holders.

A switch 38 is electrically connected to the batteries and the motor 26 for completing the electrical circuit between the batteries and the motor 26, thereby energizing the motor. In addition, the electric toothbrush of FIG. 1 might be provided with a replaceable head, as is known in the art. A suitable arrangement that can be adapted to the present invention is disclosed in U.S. Pat. No. 5,617,601.

Figure 3:
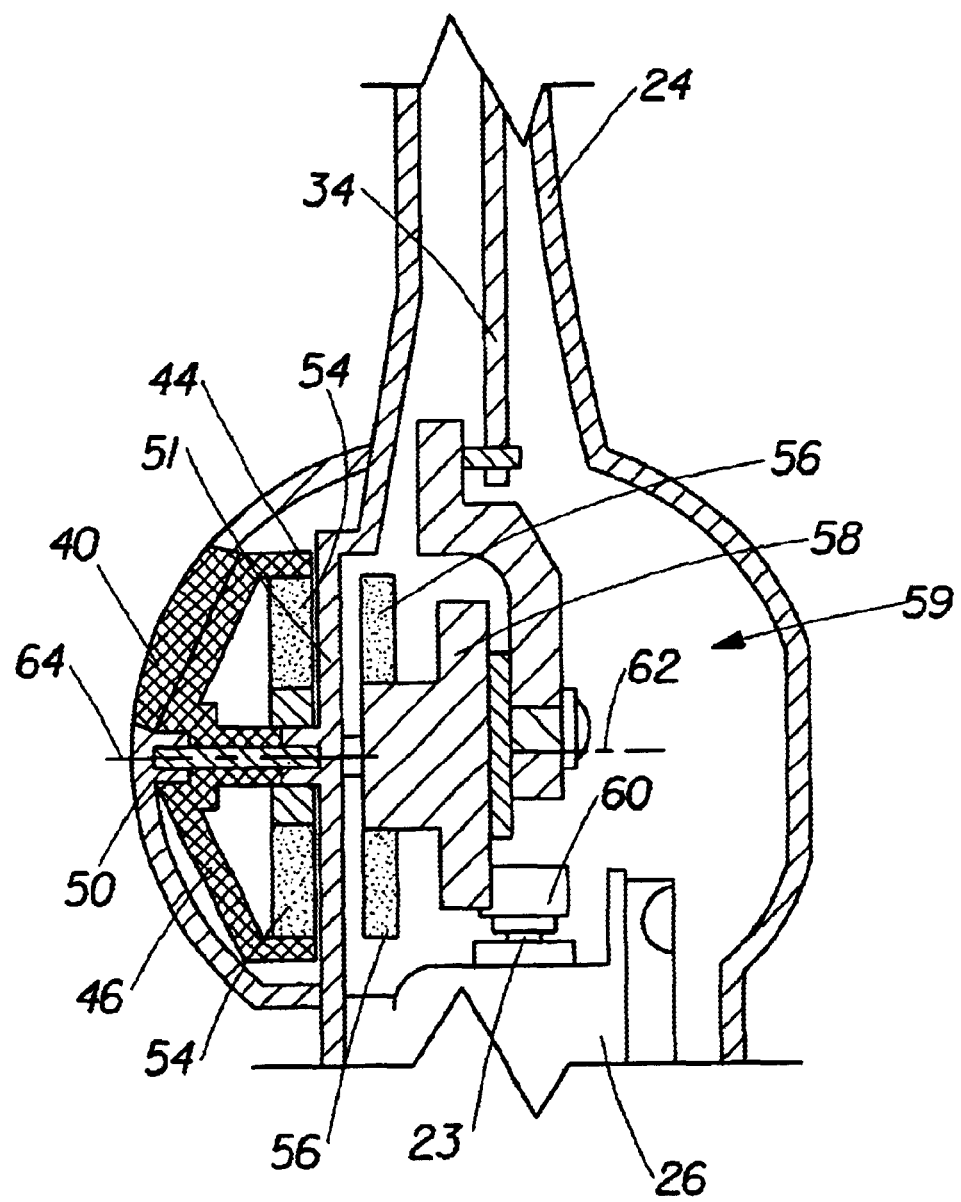
FIG. 3 is an enlarged, partial cross-sectional side view of the toothbrush of FIG. 1 taken along line 3—3 thereof.

The handle 22 includes a viewing window 40. The viewing window 40, which may be formed from a transparent plastic material, may be disposed at various locations on the handle 22, although it is desirable to place the window above the switch 38 and on the same side of the handle as the switch 38 for convenient viewing by the user. While the viewing window 40 is shown as circular, other shapes can be provided. The handle 22 may include an enlarged portion 42 adjacent the neck 24. The viewing window 40 may be disposed on or in the enlarged portion 42. The enlarged portion 42 can be provided in the form of a sphere, cylinder or other curved or curvilinear shape that is suitable for housing a movable wheel, plate, disk or other support structure 44 for a viewing surface 46, as seen in FIG. 3. The viewing surface 46 has one or more images 48 disposed thereon. At least a portion of the viewing surface is disposed beneath the viewing window 40 and is visible through the viewing window 40. The viewing window 40 can be provided in a variety of sizes. The viewing window 40 is preferably sized to allow the viewing of one or more images that are imprinted on the support structure 44. The images 48 can be text, graphics, pictures or icons, or combinations thereof. The viewing surface 46 of the support structure 44 can contain a plurality of images 48. In one embodiment, the viewing surface 46 has between 2 and 10 images. In another embodiment, the viewing surface 46 has between 2 and 6 images. The images are preferably related or share a common theme, such as a sport. For example, the images might all share the theme of soccer and include various images of a soccer player. The number of images 48 is only limited by the size of the viewing surface and the size and placement of the viewing window 40. More than one viewing window 40 can be provided if desired on the handle or enlarged portion 42. The viewing window 40 can be placed at locations other than shown in the Figs. In addition, the viewing window 40 can be colored or tinted. The viewing window can also act as a lens to magnify the images 48 on the viewing surface 46 so that they are more readily visible to a user.

Figure 4:
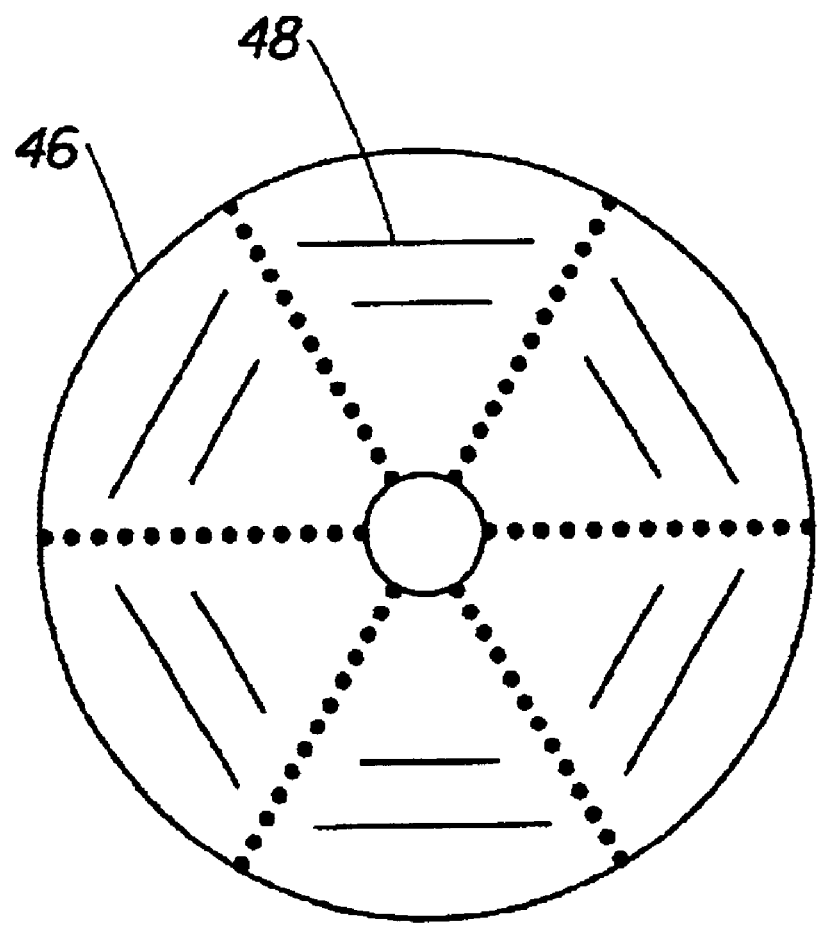
FIG. 4 is a top plan view of a viewing surface suitable of the toothbrush of FIG. 1.

Referring to FIGS. 3 and 4, an electric toothbrush having a viewing surface that is indirectly coupled to the motor 26 will now be described. The support structure 44 is rotatably mounted within the enlarged portion 42. The support structure 44 can be provided in a variety of shapes, such as a plate, disk, cylinder, etc. The viewing surface 46 may be angled in order to better orient the images 48 for viewing by a user through the viewing window 40, as seen in FIG. 3. The support structure 44 can be mounted to the enlarged portion 42 by a pin 50 that is embedded in the enlarged portion 42 and a wall 51. The support structure 44 can be mounted to the enlarged portion 42 by other means known in the art. Further, while the support structure 44 and the viewing surface thereon are illustrated as rotatably mounted, it is contemplated that other motions can be provided to the support structure 44 and/or the viewing surface 46. For example, the support structure 44 and/or viewing surface 40 might be provided with an oscillating, translating or reciprocating motion rather than a rotating motion. Still further, more than one support structure or viewing surface might be provided which move in the same or different manners. For example, one viewing surface might move in a clockwise direction while another viewing surface might move in a counter-clockwise direction. Or, one viewing surface might translate while another rotates, or two viewing surfaces might move in the same manner (i.e., both might rotate in a clockwise direction).

Disposed on a lower surface of the support structure 44 are one or more driven magnets 54. In one embodiment, the support structure 44 has between two and four driven magnets 54. Disposed opposite the driven magnets 54 are one or more driving magnets 56. The wall 51 is disposed between the driven magnets 54 and the driving magnets 56. The wall 51 forms part of the upper housing 57 of the toothbrush handle 22 and isolates the viewing surface 46 from the motor 26. Isolation of the viewing surface 46 from the motor and cavity 59 aids in maintaining the cleanliness and therefore viewability of the images 48. The driving magnets 56 are attached to a gear 58. The driving magnets 56 are preferably aligned with the driven magnets 54 so that the driving magnets 56 and driven magnets 54 are magnetically coupled such that movement of the driving magnets 56 causes a corresponding movement of the driven magnets 54. In the embodiment shown in FIG. 3, the gear 58 is rotated about an axis 62 by the motor 26 via the gear 60. The gear 58 is also operatively connected to the shaft 34 to transmit motion to the moving bristle holder 36. As the driving magnets 56 rotate about the axis 62, the driven magnets 54 are rotated in corresponding direction about axis 64 of pin 50. In this embodiment, the axes 62 and 64 are co-linear such that the gear 58 and the support structure 44 rotate about essentially the same axis. Thus, one revolution of the driving magnets 56 imparts one revolution in the same direction of the support structure 44 via the magnetic coupling of the driving and driven magnets. While the embodiment of FIG. 3 shows the driven magnets 54 as attached to the lower surface of the support structure 44, it will be appreciated that the driven magnets can be provided on a separate element which in turn is coupled to the support structure 44. For example, the driven magnets 54 might be disposed on a second gear (not shown) that in turn is coupled to the support structure 44 so that a gear reduction can be provided between the of the gear 58 and the support structure 44, in which case one revolution of the gear 58 could result in more or less than one revolution of the support structure 44 depending on the number of teeth between the gears.

In use, closing of the switch 38 completes the electrical circuit between the motor 26 and the batteries. The motor rotates the gear 60, which in turn rotates the gear 58. The driving magnets 56 rotate with the gear 58 and in turn cause the driven magnets 54 to rotate the support structure 44 and the viewing surface 46. As the viewing surface 46 rotates, images 48 are rotated into and out of view within the viewing window 40. When a user opens the switch 38 and interrupts the electrical circuit between the motor 26 and the batteries, the motor 26 will stop rotating thereby stopping rotation of the gears (i.e., 60, 62, and 58), support structure 44, and the viewing surface 46. Whichever image 48 is disposed beneath the viewing window 40 when motion stops will then be visible wholly or partially through the viewing window 40 since the image is no longer moving. Use of the toothbrush will thereby generate a random pattern of images that are visible through the viewing window 40 as the viewing surface 46 is stopped in a variety of positions beneath the viewing window 40.

Figure 5:
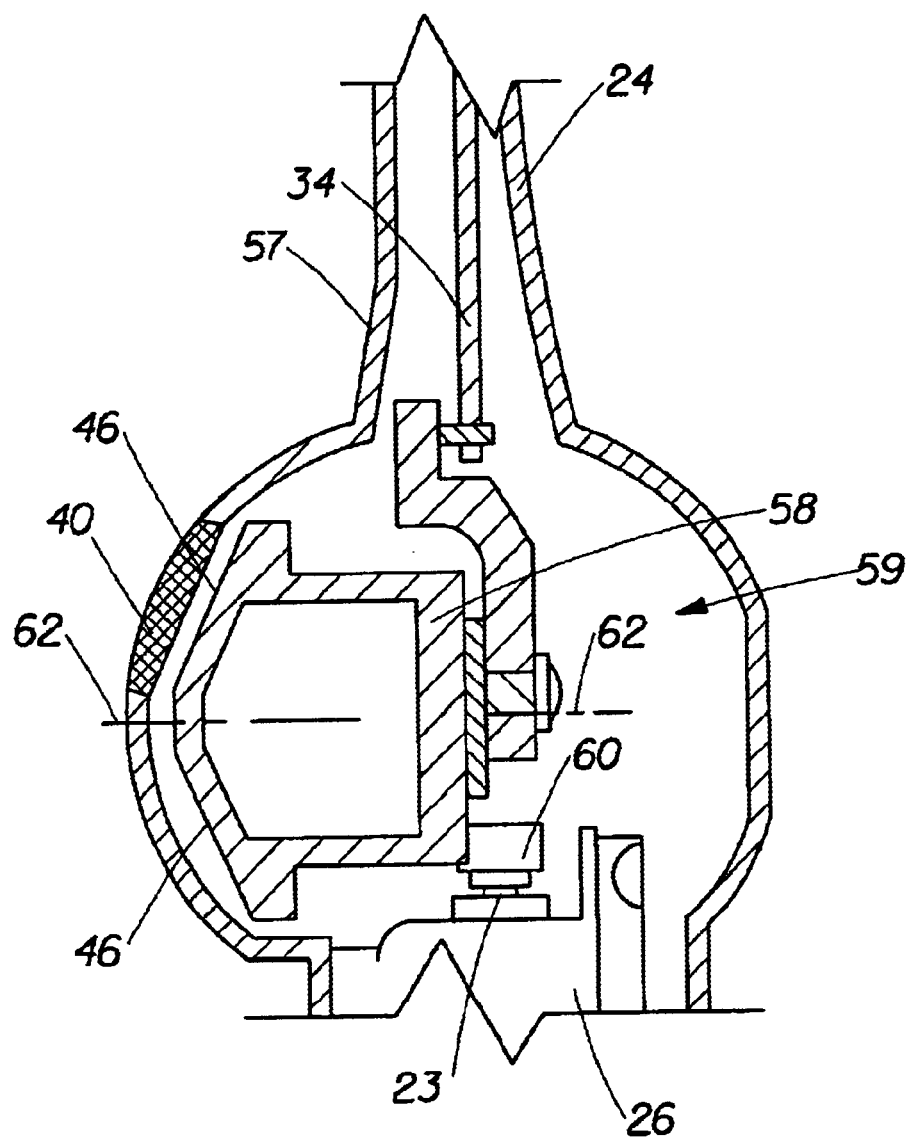
FIG. 5 is an enlarged, partial cross-sectional side view of another embodiment of the toothbrush of FIG. 1 taken along line 3—3 thereof.

While some of the embodiments discussed herein are described with respect to a viewing surface 46 that is magnetically coupled to a gear 58, it is contemplated that the viewing surface and motor 26 can be directly coupled. For example, the viewing surface and/or support structure might be pinned to the gear 58 or the viewing surface might be integrally formed as part of the gear 58, thereby eliminating the need for a separate support structure, as shown by way of example in FIG. 5. Similarly, the viewing surface might be formed on a support structure that is directly fastened to the gear 58, such as by welding, adhesives, and fasteners known in the art. In these latter embodiments, the wall 51 might be partially or completely eliminated, and the viewing surface might be coated with a protective coating (e.g., a polymer film or paste) to prevent deterioration of the images 48. Further, while the viewing surface 46 is shown disposed within an enlarged portion of the handle, it is contemplated that the viewing surface shape, size, and orientation can be changed so that the handle need not have an enlarged portion as shown in the Figures.

The present invention has been described with reference to the preferred embodiments. Obviously, modifications and alterations will occur to others upon a reading and understanding of this specification, some of which have been described herein. It is intended to include all such modifications and alterations insofar as they come within the scope of the appended claims or the equivalents thereof

What is claimed is:

1. An electric toothbrush, comprising:
    a handle having a motor disposed therein;
    a head having one or more moving bristle holders, wherein said one or more moving bristle holders are operatively connected to said motor;
    a neck disposed between said handle and said head;
    a movable shaft that is operatively connected to said motor and said one or more movable bristle holders, wherein said shaft passes through said neck;
    wherein the handle has a viewing window and a movable viewing surface disposed there beneath, wherein at least a portion of said viewing surface is visible through said window; and
    wherein said viewing surface is coupled to said motor so that rotational output of said motor causes movement of said viewing surface.

2. The electric toothbrush of claim 1, wherein said viewing surface has one or images disposed thereon.

3. The electric toothbrush of claim 1, wherein said viewing surface has between 2 and 8 images.

4. The electric toothbrush of claim 1, wherein said viewing surface is operatively coupled to a first gear that is operatively coupled to said motor.

5. The electric toothbrush of claim 4, wherein said viewing surface rotates one revolution for each revolution of said first gear.

6. The electric toothbrush of claim 4, further comprising a second gear that is operatively coupled to said motor, wherein said second gear engages said first gear.

7. The electric toothbrush of claim 1, wherein said viewing surface and said motor are magnetically coupled.

8. The electric toothbrush of claim 7, wherein said viewing surface is attached to a rotatable disk or plate.

9. The electric toothbrush of claim 8, wherein said disk has one or more driven magnets.

10. The electric toothbrush of claim 9, wherein one or more driving magnets are disposed on a first gear that is operatively coupled to said motor, wherein said one or more driving magnets are magnetically coupled to said one or more driven magnets.

11. The electric toothbrush of claim 10, wherein said first gear is operatively connected to a shaft and wherein said shaft is operatively coupled to said one or more moving bristle holders.

12. The electric toothbrush of claim 11, wherein said viewing window is disposed on an enlarged portion of said handle.

13. The electric toothbrush of claim 1, further comprising a switch that is electrically coupled to said motor and a power source, wherein closing of said switch energizes said motor thereby causing said viewing surface to rotate.

14. The electric toothbrush of claim 13, wherein said closing of said switch causes said movable bristle holders to move.

15. The electric toothbrush of claim 1, wherein said viewing surface is solid.

16. The electric toothbrush of claim 1, wherein said viewing surface has an axis of rotation and said axis of rotation is generally perpendicular to a longitudinal axis of said handle.

17. The electric toothbrush of claim 1, wherein said shaft reciprocates.

18. An electric toothbrush, comprising:
    a handle having a motor disposed therein;
    a head having one or more moving bristle holders, wherein said one or more moving bristle holders are operatively connected to said motor;
    a neck disposed between said handle and said head; and
    wherein the handle has a viewing window and a movable viewing surface disposed there beneath, wherein at least a portion of said viewing surface is visible through said window; and
    wherein said viewing surface is attached to a first gear that engages a second gear that is attached to said motor so that rotational output of said motor causes movement of said viewing surface is solid and wherein said viewing surface.

19. The electric toothbrush of claim 18, wherein said first gear is operatively connected to a shaft and wherein said shaft is operatively coupled to said one or more moving bristle holders.

* * * * *